United States Patent [19]

Hoepp et al.

[11] Patent Number: 5,688,973
[45] Date of Patent: Nov. 18, 1997

[54] PROCESS FOR THE PRODUCTION OF 2-VINYL-1,3-DIOXOLANE

[75] Inventors: Mathias Hoepp, Biebergemuend; Dietrich Arntz, Oberursel; Wolfgang Boeck, Langenselbold; Andreas Bosse-Plois, Bornheim; Klaus Raible, Frankfurt, all of Germany

[73] Assignee: Degussa Aktiengesellschaft, Frankfurt am Main, Germany

[21] Appl. No.: 523,339

[22] Filed: Sep. 5, 1995

[30] Foreign Application Priority Data

Sep. 30, 1994 [DE] Germany .................. 44 35 009.0

[51] Int. Cl.$^6$ .................................................. C07D 317/12
[52] U.S. Cl. ................................................................ 549/430
[58] Field of Search .............................................. 549/430

[56] References Cited

U.S. PATENT DOCUMENTS 3,014,924  12/1961  Brachman.
4,108,869  8/1978  Copelin.
5,216,179  6/1993  Hoepp et al..

FOREIGN PATENT DOCUMENTS 0 491 142  5/1993  European Pat. Off..

OTHER PUBLICATIONS

Piasecki, A., et al., "Reaction products of prop–2–enal with 1,2– and 1,3–diols", J. Prakt. Chem. (1987), vol. 329(4), pp. 543–554.

Fischer, R.F., et al., "Cyclic acrolein acetals", J. Org. Chem. (1960), pp. 319–324.

Piasecki, A., "Reaction products of prop–2–enal and but–2–enal with mixture: n–aliphatic alcohol and ethylene glycol", J. Prakt. Chem. (1987), vol. 329(4), pp. 579–586.

*Primary Examiner*—Nicky Chan

[57] ABSTRACT

Process for the production of 2-vinyl-1,3-dioxolane reacting acrolein with ethylene glycol in the presence of a solid, acidic catalyst and recovery of the reaction mixture. Selectivity may be increased in comparison with known prior art processes by performing the reaction in the presence of a solid acidic catalyst at a temperature of below 50° C.; the reaction mixture, from which the catalyst has been removed, is treated by extraction using an organic solvent which substantially does not dissolve ethylene glycol and has a boiling point of above 130° C.; the two phases obtained on extraction are treated for recovery by distillation and recovered educts and the organic solvent are recycled.

24 Claims, No Drawings

PROCESS FOR THE PRODUCTION OF 2-VINYL-1,3-DIOXOLANE

INTRODUCTION AND BACKGROUND

The present invention relates to a process for the production of 2-vinyl-1,3-dioxolane. The process is based upon the acid-catalyzed reaction of acrolein with ethylene glycol and is in particular suitable for the continuous production of 2-vinyl-1,3-dioxolane with elevated selectivity.

It is known to produce cyclic acetals of acrolein by reacting acrolein with the corresponding diol in the presence of a solid or dissolved acidic catalyst (*J. Org. Chem.* (1960), pages 319–324; U.S. Pat. No. 3,014,924 which is incorporated by reference in its entirety). The catalysts used in the process according to U.S. Pat. No. 3,014,924 are highly porous support materials, such as silica, silica gel, silicoaluminates, coated with mineral acids. The reaction proceeds at temperatures of between 50° and 150° C., preferably between 100° and 125° C., wherein the water of reaction is eliminated by azeotropic distillation by means of an organic solvent, such as benzene, toluene, chloroform or cyclohexane. A disadvantage of this process is the low space/time yield. The elevated reaction temperature, which is necessary due to the use of a small quantity of catalyst, entails not only a long reaction time but also the risk of secondary product formation. While an increased quantity of catalyst does indeed accelerate acetal formation, secondary products are simultaneously formed in an intolerable quantity (see *Journal für praktische Chemie* (1985), volume 327, pages 543–54). With regard to continuous operation of the process, it is not advised to use acrolein as the azeotropic entraining agent due to the consequent promotion of secondary product formation. Finally, the service life of the catalysts is too short for an industrial process as the mineral acid is dissolved off the support.

It is known from U.S. Pat. No. 4,108,869 (which is incorporated by reference in its entirety) to react acrolein using homogeneous catalysts with a 1,3-diol to yield 2-vinyl-1,3-dioxane. A mineral acid or sulphonic acids act as the catalyst. This document relates solely to the reaction of acrolein with 1,3-diols, but not of 1,2-diols. The 1,3-diol is introduced into the top of an extraction column and contains the acid. Acrolein is introduced into the middle of the column and reacts with the downwards flowing diol. A solvent (e.g., hexane) which is poorly miscible with the 1,3-diol is introduced countercurrently from the bottom. The hexane phase and the aqueous 1,3-diol phase are separated by distillation. This process cannot be satisfactorily converted for the production of 2-vinyl-1,3-dioxolane as the selectivity of the reaction is lower with ethylene glycol and the proportion of secondary products is consequently higher (with ethylene glycol, there is increased addition onto the C=C double bond of the acrolein even at room temperature). If the reaction is performed at a lower temperature, the dissipation of the heat of reaction additionally causes major problems with this manner of performing the reaction.

EP-B 0 491 142 (U.S. Pat. No. 5,216,179 which is incorporated by reference in its entirety) describes the production of cyclic acrolein glycerol acetals by reacting acrolein with glycerol on highly acidic ion exchangers. Once the pH has been adjusted, preferably to 5.5 to 6.5, the resultant reaction mixture is directly distilled. This process variant is disadvantageous in the production of 2-vinyl-1,3-dioxolane (VDL) as a water/VDL separation must be performed in the column due to the similar boiling points of water and VDL; however, at elevated temperature partial decomposition back into acrolein and ethylene glycol always occurs.

SUMMARY OF THE INVENTION

One object of the present invention is to provide a process for the production of 2-vinyl-1,3-dioxolane which overcomes the disadvantages of the prior art.

Another object is to perform a continuous process for the production of 2-vinyl-1,3-dioxolane on an industrial scale with elevated selectivity, relative to acrolein, and elevated product purity. A still further object of the invention is to be able to use a crude acrolein (i.e., an acrolein contaminated with acetaldehyde) for the reaction to form 2-vinyl-1,3-dioxolane.

A process has been found for the production of 2-vinyl-1,3-dioxolane by reacting acrolein with ethylene glycol in the presence of a solid acidic catalyst and treating the reaction mixture from which the catalyst has been removed for recovery of the desired product, which process is characterized in that the reaction is performed at a temperature of below 50° C. and the reaction mixture is extracted using a selected organic solvent. The selected organic solvent does not dissolve ethylene glycol and has a boiling point of above 130° C. The resultant aqueous phase containing ethylene glycol and the organic phase containing 2-vinyl-1,3-dioxolane are treated for product recovery by distillation.

DETAILED DESCRIPTION OF THE INVENTION

In carrying out the present invention, the reactants acrolein and ethylene glycol may be reacted in any desired manner, for example by mixing the reactants and bringing the mixture into contact with the acidic solid catalyst or by passing the mixture of acrolein and ethylene glycol over an acidic solid catalyst. The molar ratio of acrolein to ethylene glycol is not highly critical to the reaction and each of the two starting components may be used in excess. Molar ratios in the range from 5:1 to 1:5, but preferably in the range from 3:1 to 1:3, are generally used.

The process according to the present invention is performed at low temperatures in order to minimize the formation of secondary products. Low temperatures are taken to be temperatures of below 50° C. and in particular of below 15° C. (preferably 0° or above the freezing point of the reaction mixture to less than 15° C.).

The catalysts used are solid, acidic catalysts which are insoluble in the reaction mixture. Inorganic and organic ion exchangers in the acid form may in particular be used. Strongly acidic ion exchangers are preferred. Of the organic ion exchangers, ion-exchange resins based on styrene/divinylbenzene copolymers with sulphonate or phosphonate groups are particularly suitable, wherein such resins with more strongly acidic sulphonate groups are preferred. Conventional commercial perfluorinated sulphonic acid resins may also be used. Of the inorganic ion exchangers, acidic or strongly acidic zeolites, such as those of the H-ZSM type, may in particular be cited. Such ion exchangers are well known in the art and any of those shown in U.S. Pat. No. 5,216,179 may be used.

The process according to the present invention may be performed discontinuously, for example in a tubular reactor, or continuously, for example in a loop reactor, wherein the catalyst may be arranged as a fixed bed or fluidized bed; in principle, any reactor type which ensures sufficient contact between the reaction mixture and the solid catalyst is suitable. Such reactors are well known in the art.

When the process is performed continuously, acrolein and ethylene glycol in the desired molar ratio are preferably continuously introduced into a reaction mixture containing acrolein, ethylene glycol, 2-vinyl-1,3-dioxolane and water, preferably an equilibrium reaction mixture, and, after passing through the catalyst bed, the corresponding quantity of reaction mixture is drawn off for recovery of the product. The contact time of the reaction mixture, which is expressed as the LHSV value (liquid hourly space velocity), should assume an LHSV value of between 1 and 30 $h^{-1}$, preferably between 3 and 15 $h^{-1}$.

After the reaction, the reaction mixture substantially consists of 2-vinyl-1,3-dioxolane together with the reactants acrolein and ethylene glycol and the water of reaction. The term "substantially" is taken to mean that the reaction mixture additionally contains secondary products, principally the adduct of ethylene glycol onto 2-vinyl-1,3-dioxolane, 2-(5'-hydroxy-3'-oxopentyl)-1,3-dioxolane. The composition of the reaction mixture is determined by the selected molar ratio of acrolein to ethylene glycol and the reaction temperature, and preferably corresponds to the particular prevailing equilibrium composition.

After the reaction, if necessary, the reaction mixture, from which the catalyst has been removed, is adjusted using a basic substance, such as a trialkanolamine, to a pH value of 4.5 to 7, preferably of 5.5 to 6.5, determined after 10 times dilution with water, and then extracted with an apolar to slightly polar organic solvent. This partial neutralisation is rarely necessary. The solvent should substantially not dissolve ethylene glycol and the boiling point of the solvent should be above 130° C., preferably above 150° C. Suitable organic solvents are aliphatic linear or branched hydrocarbons, such as n-$C_{10}$ to $C_{12}$ alkanes or so-called isoparaffins (isoalkanes) with a boiling point in the range from 170° to 250° C.; cycloaliphatic hydrocarbons, such as decalin, together with monoalkyl- or polyalkyl-substituted aromatic hydrocarbons, such as di-, tri- and tetramethylbenzene, are also suitable extracting agents. Conventionally, 0.3 to 3 parts by volume of organic solvent are used per part by volume of reaction mixture. On extraction, an aqueous phase containing water and ethylene glycol together with high-boiling secondary products and an organic phase containing 2-vinyl-1,3-dioxolane, acrolein and organic solvent are formed, which are separated from each other in a known manner.

If required, it may be convenient to pass the aqueous phase and/or the organic phase containing 2-vinyl-1,3-dioxolane through a coalescer in order to ensure sufficient separation of any still dispersed very fine droplets of the other phase and so obtain very pure phases. Particularly pure phases are obtained with coalescers if 1 to 10 vol. % of the already dispersed phase are added to the phase to be purified before it is passed through the coalescer, i.e., water is added to the organic phase and organic solvent to the aqueous phase.

If an extraction column is used, this is conveniently operated in such a manner that the reaction mixture is introduced into the upper part. In order to improve phase separation, 0.01 to 1 part by volume of water per part by volume of reaction mixture is introduced into the top of the extraction column or directly into the reaction mixture to be extracted. 0.3 to 3 parts by volume of extracting agent per part by volume of reaction mixture are introduced at the bottom of the extraction column.

After extraction and phase separation, acrolein is first distilled off from the organic phase and then the product; if the process is performed continuously, the high-boiling extracting agent is directly introduced (i.e., without distillation) into the extraction. Acrolein is first distilled off from the aqueous phase, then the water of reaction and finally the ethylene glycol. The high-boiling secondary products and the water of reaction are discharged; the unreacted educts (acrolein and ethylene glycol) recovered from the two phases are returned to the reaction stage.

One advantage of the invention consists in the possibility of using so-called crude acrolein for the reaction. In addition to the customary 3.5 wt. % of water, this crude acrolein also contains 2 wt. % of acetaldehyde. The contaminant acetaldehyde is quantitatively converted into the corresponding acetal, 2-methyl-1,3-dioxolane, during the reaction. On extraction, this compound passes into the organic phase and must be additionally separated by distillation. In this case, the organic phase is treated in such a manner that the acrolein is first distilled off, then the 2-methyl-1,3-dioxolane and finally the 2-vinyl-1,3-dioxolane.

The process according to the present invention is distinguished by the fact that the 2-vinyl-1,3-dioxolane may be obtained with surprisingly high selectivity, namely of around 90% and sometimes higher, relative to the acrolein. According to *J. Prakt. Chem.* (1987), volume 329(4), pages 579–586, the reaction of ethylene glycol with acrolein in fact results in a complex reaction mixture, the principal constituent of which is 2-(5'-hydroxy-3'-oxopentyl)-1,3-dioxolane. The process may be performed on an industrial scale with a long catalyst service life. Unreacted educts may be simply recovered and added to a subsequent batch. The solvent used for the extraction may be recycled without requiring distillation.

The following examples are illustrative of the invention:

EXAMPLE 1

A fixed catalyst bed with 2 l of a strongly acidic ion exchanger (K 2431 from Bayer) is fitted in a loop reactor with a total volume of 40 l. A reaction mixture of the approximate composition 34 wt. % acrolein, 36 wt. % ethylene glycol, 23 wt. % 2-vinyl-1,3-dioxolane, 4 wt. % water and 3 wt. % secondary products is continuously pumped around the circuit at an internal temperature of 5° C. 4.6 kg/h of acrolein and 5 kg/h of ethylene glycol are continuously introduced and the corresponding quantity of reaction mixture (9.6 kg) drawn off (LHSV=4.8). The discharged reaction mixture is introduced into the top of the extraction column together with 1 kg/h of water. 7.3 l/h of decane are introduced countercurrently into the bottom of the extraction column. The discharged organic phase and aqueous phase are subjected to fractional distillation, wherein acrolein and then the product are distilled off from the organic phase. Acrolein is likewise first distilled off from the aqueous phase, then water and then ethylene glycol. The following hourly quantities are obtained: 3.3 kg of acrolein, 3.5 kg of ethylene glycol, 2.1 kg of 2-vinyl-1,3-dioxolane, 0.4 kg of water and 0.3 kg of high-boiling components. Conversion of the introduced acrolein is 28.3% with a selectivity of 94.2% and conversion of the introduced ethylene glycol is 30.0% with a selectivity of 86.8%.

EXAMPLE 2

The process is carried out analogously to example 1, but the introduced acrolein consists of 1.6 kg of crude acrolein containing 94.5 wt. % of acrolein, 3.5 wt. % of water and 2 wt. % of acetaldehyde, together with 3 kg of recycled acrolein (96% acrolein, 4% water).

The resultant reaction mixture has the following composition: 31 wt. % acrolein, 34 wt. % ethylene glycol, 23 wt. % 2-vinyl-1,3-dioxolane, 1.6 wt. % 2-methyl-1,3-dioxolane, 4 wt. % water and 3 wt. % secondary products.

After recovery by distillation, the following hourly quantities are obtained: 3.2 kg of acrolein, 3.4 kg of ethylene glycol, 2.1 kg of 2-vinyl-1,3-dioxolane, 0.15 kg of 2-methyl-1,3-dioxolane, 0.4 kg of water and 0.3 kg of high-boiling components. The recovered acrolein and ethylene glycol are reused. Conversion of the introduced acrolein is 30.1% with a selectivity of 89.1% and conversion of the introduced ethylene glycol is 32% with a selectivity of 81.3%.

COMPARATIVE EXAMPLE

Production of VDL according to U.S. Pat. No. 3,014,924

372 g of ethylene glycol, 750 ml of benzene, 2.7 g of catalyst (0.5% $H_2SO_4$ on silica gel) and 120 g of acrolein are initially introduced into an apparatus with an azeotropic separator. The mixture is then heated to boiling while being stirred and the entrained water is separated. Over a period of 4 hours, a further 250 g of acrolein are apportioned in such a manner that the internal temperature remains between 71° and 74° C. The mixture is then further heated until the internal temperature reaches 86° C. Total reaction time is 12 h, a total of 123 ml of water are separated. After cooling, the reaction mixture is filtered and fractionally distilled. 533 g of 2-vinyl-1,3-dioxolane are obtained (89% yield).

Further variations and modifications of the foregoing will be apparent to those skilled in the art and such variations and modifications are intended to be encompassed by the claims that are appended hereto.

German Priority Application P 44 35 009.0 filed 30 Sep. 1994 on is relied on and incorporated by reference in its entirety.

We claim:

1. A process for the production of 2-vinyl-1,3-dioxolane, comprising reacting acrolein with ethylene glycol at a temperature of below 50° C. in the presence of a solid acidic catalyst to form a reaction mixture, removing said catalyst to form a catalyst-free reaction mixture, extracting said catalyst-free reaction mixture with an organic solvent wherein the resulting aqueous phase contains ethylene glycol and the resulting organic phase contains 2-vinyl-1,3-dioxolane.

2. The process according to claim 1, further comprising recovering said 2-vinyl-1,3-dioxolane by distillation.

3. The process according to claim 1, wherein said temperature is less than 15° C.

4. The process according to claim 3, wherein said temperature is 0° to less than 15° C.

5. The process according to claim 1, wherein said organic solvent does not dissolve ethylene glycol.

6. The process according to claim 1, wherein said organic solvent has a boiling point of above 130° C.

7. The process according to claim 6, wherein said organic solvent has a boiling point of above 150° C.

8. The process according to claim 1, wherein said organic solvent is selected from the group consisting of an aliphatic linear hydrocarbon, an aliphatic branched hydrocarbon, a cycloaliphatic hydrocarbon, a monoalkyl-substituted aromatic hydrocarbon, a polyalkyl-substituted aromatic hydrocarbon, and mixtures thereof.

9. The process according to claim 8, wherein said organic solvent is selected from the group consisting of n-$C_{10}$ to $C_{12}$ alkanes, isoparaffins with a boiling point in the range from 170° to 250° C., decalin, dimethylbenzene, trimethylbenzene, and tetramethylbenzene.

10. The process according to claim 1, wherein the molar ratio of said acrolein to said ethylene glycol is 5:1 to 1:5.

11. The process according to claim 10, wherein the molar ratio of said acrolein to said ethylene glycol is 3:1 to 1:3.

12. The process according to claim 1, further comprising prior to said extracting combining said catalyst-free reaction mixture with such a quantity of a basic substance which raises the pH value of said catalyst-free reaction mixture that the pH value, measured in a 10 times dilution with water, is in the range between 4.5 and 7.

13. The process according to claim 12, wherein said range is 5.5 and 6.5.

14. The process according to claim 12, wherein said basic substance is a trialkanolamine.

15. The process according to claim 1, wherein said extracting is performed using at least one extraction column, wherein 0.01 to 1 part by volume of water per part by volume of said catalyst-free reaction mixture is apportioned to the top of said column or to said catalyst-free reaction mixture introduced into the upper part of said column.

16. The process according to claim 15, wherein 0.3 to 3 parts by volume of said solvent per part by volume of said catalyst-free reaction mixture are introduced at the bottom of said extraction column.

17. The process according to claim 1, wherein said acrolein contains about 3.5 wt. % water and about 2 wt. % acetaldehyde.

18. The process according to claim 1, wherein 0.3 to 3 parts by volume of said organic solvent are used per part by volume of catalyst-free reaction mixture.

19. A process for the production of 2-vinyl-1,3-dioxolane comprising continuously adding acrolein and ethylene glycol into an equilibrium reaction mixture containing 2-vinyl-1,3-dioxolane, ethylene glycol, acrolein and water to form a reaction mixture, passing said reaction mixture over an acidic fixed bed catalyst, discharging and extracting a quantity of said reaction mixture corresponding to said acrolein and said ethylene glycol to be distilled and recycling the remaining quantity of said reaction mixture; wherein said process is conducted at a temperature of below 50° C.

20. The process according to claim 19, wherein the contact time of said reaction mixture is an liquid hourly space velocity value of between 1 and 30 $h^{-1}$.

21. The process according to claim 20, wherein the contact time of said reaction mixture is an liquid hourly space velocity value of between 3 and 15 $h^{-1}$.

22. The process according to claim 2 wherein the catalyst-free reaction mixture is adjusted to a pH of from about 4.5 to 7 before extraction, the pH being measured in a 10 times dilution with water.

23. The process according to claim 1 wherein the solvent is a linear or branched aliphatic hydrocarbon having 10 to 12 carbon atoms.

24. The process according to claim 1 wherein the acrolein is crude acrolein.

* * * * *